United States Patent [19]

Baker

[11] Patent Number: 4,780,320

[45] Date of Patent: Oct. 25, 1988

[54] CONTROLLED RELEASE DRUG DELIVERY SYSTEM FOR THE PERIODONTAL POCKET

[75] Inventor: Richard W. Baker, Menlo Park, Calif.

[73] Assignee: Pharmetrix Corp., Menlo Park, Calif.

[21] Appl. No.: 856,961

[22] Filed: Apr. 29, 1986

[51] Int. Cl.$^4$ .............................................. A61L 15/03
[52] U.S. Cl. .................................. 424/493; 424/486; 424/497
[58] Field of Search ............... 424/493, 489, 484, 490, 424/486, 497

[56] References Cited

U.S. PATENT DOCUMENTS

| | | |
|---|---|---|
| 3,185,625 | 5/1965 | Brown . |
| 3,972,995 | 8/1976 | Tsuk et al. ............................ 424/28 |
| 4,039,653 | 8/1977 | Defoney et al. ...................... 424/14 |
| 4,059,686 | 11/1977 | Tanaka et al. ........................ 424/19 |
| 4,226,848 | 9/1980 | Nagai et al. ........................... 424/19 |
| 4,250,163 | 2/1981 | Nagai et al. ........................... 424/14 |
| 4,369,172 | 2/1983 | Schor et al. ........................... 424/19 |
| 4,434,153 | 2/1984 | Urquhart et al. ..................... 424/469 |
| 4,568,535 | 2/1986 | Loesche ................................ 424/19 |
| 4,568,536 | 2/1986 | Kronenthal et al. . |
| 4,569,837 | 2/1986 | Suzuki et al. ......................... 424/28 |
| 4,585,651 | 4/1986 | Beck et al. . |
| 4,597,960 | 7/1986 | Cohen . |
| 4,622,244 | 11/1986 | Lapka et al. . |
| 4,650,665 | 3/1987 | Kronenthal et al. . |
| 4,652,441 | 3/1987 | Okada et al. . |

OTHER PUBLICATIONS

J. Slots, "Subgingival Microflora + Periodontal Disease," *J. Clin. Periodontol*, 6, 315 (1979).

S. S. Socransky, "Microbiology of Periodontal Disease-Present Status and Future Considerations," *J. Periodontol.* 48, 497 (1977).

*Primary Examiner*—Nancy A. B. Swisher
*Attorney, Agent, or Firm*—J. Farrant

[57] ABSTRACT

A controlled release drug delivery system for placement in the periodontal pocket. The system comprises a plurality of drug-containing microparticles or microcapsules, between 10 and 500 microns in size, suspended in a pharmaceutically acceptable carrier medium, and is capable of maintaining an effective level of drug in the periodontal pocket for a period of 1 to 30 days.

12 Claims, 5 Drawing Sheets

CONTROLLED RELEASE DRUG DELIVERY SYSTEM FOR THE PERIODONTAL POCKET

This invention was made with Government support under Grant No. 1-R43-DE07022-01 awarded by the National Institute of Dental Research. The Government has certain rights in this invention.

BACKGROUND OF THE INVENTION

1. Field of the Invention

This invention relates to a controlled release system of drug delivery to the periodental pocket. Such a system can be used to treat any periodontal disease, such as gingivitis, pyorrhea alveolaris and other related disorders.

2. Description of the Prior Art

Periodontal disease, with caries, is the most important cause of loss of teeth. It is well established that bacteria are directly involved in both the onset and progression of periodontal disease. See for example J. Slots, "Subgingival Microflora and Periodontal Disease," *J. Clin. Periodontal.* 6, 315 (1979) and S. S. Socransky, "Microbiology of Periodontal Disease—Present Status and Future Considerations," *J. Periodontol.* 48, 497 (1977). This has led to the widespread use of antibiotics in the treatment of periodontal disease, and particularly to the use of tetracycline, since significantly higher levels of tetracycline are found in gingival fluid than in blood after administration of single or multiple oral doses. (J. M. Gordon et al., "Sensitive Assay for Measuring Tetracycline Levels in Gingival Crevice Fluid," *Antimicrob. Agents Chemother.* 17, 193 (1980), J. M. Gordon et al., "Concentrations of Tetracycline in Human Gingival Fluid after Single Doses," *J. Clin. Periodontol.* 8, 117 (1981) and J. M. Gordon et al., "Tetracycline: Levels Achievable in Gingival Crevice Fluid and in vitro Effect on Subgingival Organisms. Part 1. Concentrations in Crevicular Fluid after Repeated Doses," *J. Periodontal.* 52, 609 (1981).) However the typical effective tetracycline oral dose of one gram per day for 30 days can lead to serious side effects. It has been estimated that the dose should be of the order of one hundred times smaller to avoid these effects. A more satisfactory approach then is to administer the antibiotic topically using a controlled release device to sustain an effective dose for the required length of time. Because the drug is delivered locally, a much reduced dose will suffice for effective therapy, and harmful side effects can be reduced or eliminated.

Long lasting drug delivery systems presently used in the oral cavity fall broadly into two groups; either troches, pastilles or tablets which adhere to the oral mucosa in some way, or drug containing strips or dosage forms which are attached to the gums, teeth or other interior surface of the mouth. A good example of the former category is U.S. Pat. No. 4,039,653. This patent discloses a sustained release tablet coated with a pharmaceutically acceptable oral adhesive, which is placed in an upper corner of the mouth and is capable of dispensing an odor-masking agent, local anaesthetic or other medication in a sustained fashion for periods of up to twelve hours. U.S. Pat. No. 4,250,163 discloses a method of administering a broad range of medications to the oral cavity by means of a water-swellable and mucosa-adhesive polymeric matrix, which can be in the form of a tablet, powder or granules and which is effective for times of the order of a few hours. As can be seen from these and other examples, such as U.S. Pat. Nos. 4,226,848, 4,369,172 and 4,059,686, such troches and tablets are normally effective for period of hours rather than days, and a course of treatment lasting one month would require the use of numerous tablets. Furthermore they are inappropriate to the treatment of periodontal disease because the drug is released into the saliva or oral mucosa, and does not penetrate the periodontal pocket to any significant extent. Buccal tapes, strips and forms suffer from the same disadvantages. For example, the buccal dosge form disclosed in U.S. Pat. No. 3,972,995 was found to be effective without leaking, if not wrinkled or dislodged by the teeth, for about one hour only. This highlights another disadvantage of existing methods of dispensing drugs for oral therapy; they may slip or be dislodged by the tongue or teeth, may be uncomfortable to a greater or lesser degree, and may interfere with the normal oral functions to some extent. Recent developments in the art are directed toward delivering the therapeutic agent directly to the periodontal pocket, in some cases in a controlled release formulation. Gordon et al. have described the use of a drug-filled polymer hollow fiber. (J. M. Goodson et al., "Periodontal Therapy by Local Delivery of Tetracycline," *J. Clin. Periodontal.* 6, 83 (1979), J. Lindhe et al., "Local Tetracycline Delivery Using Hollow Fiber Devices in Periodontal Therapy," *J. Clin. Periodontol.* 6, 141 (1979) and R. L. Dunn et al., "Monolithic Fibers for Controlled Delivery of Tetracycline," in *Proc. Ninth Int. Symposium on Controlled Release of Bioactive Materials,* Ft. Lauderdale, Fl., July (1982).) This device is tied around a tooth and gently pressed below the margin of the gingiva so that it resides in the periodontal pocket, and is capable of delivering an effective dose of 2.5 micrograms of tetracycline per day per periodontal pocket for a prolonged period of a week or more. Similar results have been obtained by Coventry and Newman (J. Coventry and H. N. Newman, "Experimental Use of a Slow Release Device employing Chlorhexidine Gluconate in Areas of Acute Periodontal Inflammation," *J. Clin. Periodontol.* 9, 129 (1982)) and Addy et al. (M. Addy et al., "The Development and in vitro Evaluation of Acrylic Strips and Dialysis Tubing for Local Drug Delivery," *J. Periodontol.* 53, 693 (1982)) using acrylic strips 1 mm or more long, impregnated with chlorohexidine, tetracycline or metronidazole, which were inserted into the periodontal pocket with tweezers. Such a strip, formed from ethylcellulose impregnated with metronidazole, is disclosed by Loesche in U.S. Pat. No. 4,568,538 (February 1986). Another strip, employing a water soluble polymer of a particular elasticity and viscosity, is disclosed by Suzuki et al. in U.S. Pat. No. 4,569,837. Although these devices may be able to dispense an appropriate drug for a time span of a week or more, they are inappropriate to widespread use because they are difficult and time consuming to apply and may be dislodged by the patient during normal oral functions.

The drug releasing microparticle system that is proposed below overcomes all of these previous difficulties, and provides a drug formulation which is easily applied and capable of delivering antibiotics or other drugs reliably to the periodontal pocket for a prolonged period of time, without interfering in any way with the normal oral functions.

SUMMARY OF THE INVENTION

This invention is a controlled release drug delivery system for placement in the periodontal pocket. The system comprises microparticles or microcapsules, hereinafter referred to as microparticles, suspended in a pharmaceutically acceptable carrier medium. The microparticles are between 10 and 500 microns in size, and consist of an active agent dispersed within or encapsulated by a rate-controlling polymer matrix.

Microparticles of this specification can be prepared by a variety of well-established techniques, for example solvent evaporation, coacervation or spray-drying. The active agent may be one of a broad spectrum of drugs, including, but not limited to, antibiotics, anti-inflammatory agents, local anaesthetics and so on. The polymer matrix may be chosen from a range of medically suitable materials and varied to provide the required release rate for the drug involved. Embodiments employing biodegradable polymers can limit the life of the microparticles to a month or two and prevent microparticle entrapment in the periodontal pocket for excessive periods of time.

The carrier medium may be an aqueous solution, paste or gel. In general the properties required are that it should be pharmaceutically acceptable (non-toxic and non-allergenic), promote good adhesion in the periodontal pocket, and have a high permeability for the active agent involved. A preferred embodiment of the invention employs a thermally gelling polymer such as Pluronic ®F127 from BASF Wyandotte. In aqueous solution this polymer is a free-flowing fluid at room temperature, but gels rapidly above 30° C. Embodiments of the invention are introduced into the periodontal pockets of the patient by a dentist or physician using a syringe and a fine rubber tube. The system then resides in the pocket, unfelt by the patient and reliably delivering a steady dose of the chosen medication.

An object of the invention is to provide a system to deliver a drug or other active agent to the periodontal pocket at a steady dosage level which can be sustained for a period of days or weeks.

Another object of the invention is that the said system should be comfortable in use, should not interfere with the normal oral functions and should not be easily dislodged by the patient.

A further object is that the said system should be capable of insertion in a simple manner, and should not require the use of undue time or exceptional expertise on the part of the dentist or physician involved.

Other objects and advantages of the present invention will be apparent from the following description.

DETAILED DESCRIPTION OF THE INVENTION

"Active agent" as used herein broadly includes any composition or compound of matter which when dispensed in the chosen environment of use produces a predetermined, beneficial and useful result.

"Drug" as used herein broadly includes physiologically or pharmacologically active substances for producing a localized effect at the administration site or a systemic effect at a site remote from the administration site.

Figure 1A:
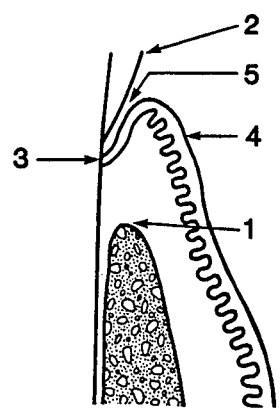
FIG. 1A shows the normal human gingival sulcus.
Figure 1B:
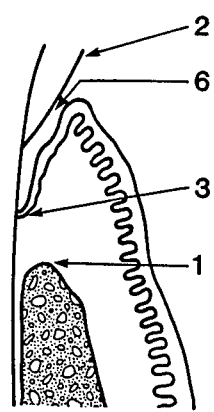
FIG. 1B shows the effect of periodontal disease, where the sulcus has deepened to form a periodontal pocket.

Refering now to FIG. 1, FIG. 1A shows the normal human gingival sulcus. The alveolar bone crest 1 is undamaged. The depth from the crown 2 to the epithelial attachment 3 is around 2 or 3 mm. Between the crown 2 and the free gingiva 4 is the healthy gingival sulcus 5. In contrast FIG. 1B shows the effect of periodontal disease. The alveolar bone crest 1 has been eroded; the depth from the crown 2 to the epithelial attachment 3 has increased considerably, and the normal sulcus has deepened to form a periodontal pocket 6.

Suitable drugs which can be administered in the drug delivery system of the present invention include but are in no way limited to antibacterial agents such as thimerosal, chloramine, boric acid, phenol, iodoform, chlorhexidine and other oral antiseptics, $\beta$-lactam antibiotics, for example cefoxitin, n-formamidoyl thienamycin and other thienamycin derivatives, tetracyclines, chloramphenicol, neomycin, gramicidin, kanamycin, amikacin, sismicin and tobramycin; anti-inflammatory steroids such as cortisone, hydrocortisone, beta-methasone, dexamethasone, fluocortolone, prednisolone, triamcinolone and the like; non-steroidal anti-inflammatory drugs including flurbiprofen, ibuprofen, indomethacin, piroxicam, naproxen, antipyrine, phenylbutazone and aspirin for example; plaque dissolving substances, for example lysozyme chloride or amylase; and local anaesthetics such as lidocaine, procaine, benzocaine, xylocaine and so on.

The system comprises a plurality of microparticles or microcapsules between 10 and 500 microns in size, suspended in a pharmaceutically acceptable carrier. Microcapsules in this context are defined as reservoir systems in which a simple reservoir of active agent is surrounded by a membrane shell; microparticles are small monolithic entities in which the active agent is randomly dispersed through the particle matrix. Many practical formulations fall between these two definitions; for example microcapsules often agglomerate during the microencapsulation process, while the size of the active agent particles contained in a microparticle system is often of the same order as the size of the microparticles themselves. In the following discussion then, "microparticle" will be defined to mean microparticle, microcapsule or any intermediate form. Various physical and chemical methods for preparing microparticles have been developed over the past twenty years and the technology is well established and well documented. See for example Patrick B. Deasy, *Microencapsulation and Related Drug Processes*. Marcel Dekker Inc., New York, 1984. The more important methods are described below, and depending on the chemical and physical properties of the desired embodiment, any of these could be used to prepare the microparticles.

Coacervation was the first microencapsulation technique and remains one of the most widely used. Coacervation usually involves four steps. First a dispersion or emulsion of the active agent is prepared in an aqueous polymer solution. Secondly, the polymer is caused to precipitate slowly by some means: addition of a non-solvent, cooling, change of pH or ionic strength, or addition of an incompatible polymer solution for example. Under these conditions, most polymers initially precipitate as a highly swollen liquid polymer phase, this phenomenon being known as coacervation. During the precipitation, the liquid phase coats the dispersed active agent droplets. Finally the microparticles thus formed are separated from the solvent/non-solvent mixture, dried and sieved into different size fractions. Most industrial coacervation processes use aqueous solutions of gelatin and other water soluble polymers and can only encapsulate hydrophobic, water insoluble agents dissolved in an organic solvent. However the process can be inverted by using organic-solvent-soluble polymers with organic-solvent-insoluble active agents dissolved in an aqueous solution. Since many drugs are at least moderately water soluble, this makes the process appropriate to the preparation of microencapsulated pharmaceuticals. For example ethylcellulose has been used to prepare microparticles containing aspirin, indomethacin, paracetamol, theophylline and vitamins among others. The main disadvantage of the coacervation technique is that is requires considerable skill to produce particles with consistent properties, since the particle sizes and wall thickness may vary widely.

Interfacial polymerization occurs when two reactive monomers, each in different immiscible liquids, are brought into contact. The monomers are able to react only at the interface of the two solutions, where a polymer film forms. When one solution is dispersed in the other, the polymer film formed encapsulates the disperse phase. This process is not widely used for the commercial preparation of pharmaceuticals because of various practical problems; toxicity of remaining unreacted monomer, drug degradation as a result of reaction with the monomer, high permeability of the encapsulating polymer to the active agent involved, fragility of the capsules produced and non-biodegradability of the particles amongst others. However extensive research work has been done on the coating of high-molecular-weight biological materials such as enzymes with polyamides, and recently McGinity et al. have successful encapsulated caffeine, sodium salicylate, theophylline and other drugs in a nylon coated particle by this technique. (J. W. McGinity et al., "Influences of matrices on nylon-encapsulated pharmaceuticals," *J. Pharm. Sci.* 70, 372–375 (1981).)

Solvent evaporation is another technique which is appropriate for the encapsulation of a water-soluble drug. First the polymer matrix material is dissolved in an organic solvent. Adding the active agent, dissolved in water, and emulsifying, produces a water-in-oil emulsion. This emulsion is re-emulsified in an aqueous solution, forming a water-in-oil-in-water emulsion. This final aqueous solution usually contains a polymer such as gelatin, to prevent aggregation. the solvent is then removed under reduced pressure to form a hard outer wall to the particles. Hydrophobic agents may also be prepared by solvent evaporation, but in this case the procedure is modified by first preparing an oil-in-water emulsion of the agent. This process has been used for example by Wakiyama et al. to prepare microparticles of butamben, tetracaine and dibucaine, where the polymer material used was polylactic acid in a solution of methylene chloride, methyl acetate or ethyl acetate. (N. Wakiyama et al., "Preparation and evaluation in vitro of polylactic acid microspheres containing local anaesthetics," *Chem. Pharm. Bull.* 29, 3363–68 (1981).) Recently Kojima et al. used the solvent evaporation technique to enclose various local anaesthetics in polycarbonate microspheres: sustained drug-release times measured in hundreds of hours resulted. (*Chem. Pharm. Bull.* 32, 2795–2802 (1982).)

Finally a number of simple physical techniques can be used to prepare microparticles, and spray drying, for example, is widely used in the preparation of food or pharmaceutical flavors. Spray dried particles are less satisfactory for preparing drugs however, as the particles tend to be non-uniform and the coating porous, causing the active agent to disperse too rapidly for a controlled-release application. However, several penicillins have been microencapsulated in ethylcellulose in this way. See for instance U.S. Pat. No. 4,016,254 (April 1977).

The polymer matrix material chosen should be pharmaceutically acceptable, soluble in a variety of suitable solvents and available in different grades to enable the release rate of the active agent to be controlled. Cellulose acetate and ethyl cellulose have a good record of acceptability in medical applications. Polystyrene, polysulfone and polycarbonate are possible choices for use with antibiotics such as tetracycline. Experiments described in the Examples below showed that tetracycline release from polysulfone and polystyrene was extremely slow, and that polycarbonate release values were much more satisfactory; however different results could well be obtained with different drugs. Biodegradable polymers such as the lactic-glycolic acid copolymers from Hexel Corporation of Hayward, Calif. offer a distinct advantage, in that they have been found to biodegrade over a period of 4 to 12 weeks, and thus could prevent particles becoming trapped in the periodontal pocket indefinitely. Work on the use of such polymers for controlled release drug dispensing has been carried out by several researchers. (For example, D. A. Wood, *Int. J. Pharmaceut.* 7, 1 (1980). A paper of Setterstrom et al. in Polym. Mater. Sci. Eng., 53, 620–626 (1985) describes the use of ampicillin microencapsulated in poly(DL-lactide-co-glycolide) for topical application to wounds; effective levels of antibiotic are detectable at the wound site for at least fourteen days. The size of the microparticles should be limited to between 10 and 500 microns. Very small particles with consistent properties are difficult to prepare and they may wash out of the periodontal pocket rather easily. Particles larger than 500 microns may be too large to deliver with syringe and rubber tube and may be uncomfortable or irritating to the gingival membranes.

The theory of drug release from solid microspheres was developed by Higuchi (T. Higuchi, *J. Pharm. Sci.* 52, 1145 (1963)). The release is controlled by the equation $$\frac{3}{2}\left(1 - \left[1 - \frac{M_t}{M_\infty}\right]^{\frac{2}{3}} - \frac{M_t}{M_\infty}\right) = \frac{3P \cdot t}{r_o^2 C_o}$$

$M_t/M_\infty$ is the fraction of total drug released after time t from a particle of radius $r_o$. The drug permeability in the matrix is P and the drug loading is $C_o$. This equation can be used to limit further the size of the microparticles, and to select an appropriate drug loading, so that the desired dosage level and release rate for the chosen embodiment is obtained.

Figure 2:
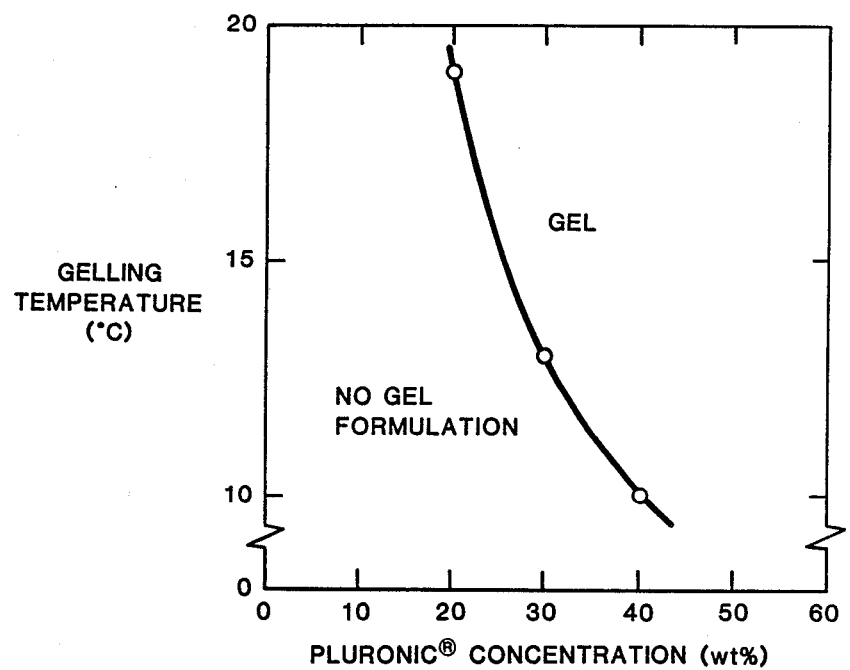
FIG. 2 is a graphic representation of the gelling characteristics of aqueous Pluronic F127 solutions.

The carrier medium used to contain the microparticles must conform to several requirements. First it should be biocompatible, non-toxic and non-allergenic. Secondly it should have a low solubility but a high permeability for the drug in question. A low solubility is necessary to minimize leaching of the drug from the microparticle during storage. High permeability is required in order that the drug be well conducted from the microparticle to the mucous membranes. Thirdly it should promote good adhesion of the microparticles in the periodontal pocket, and last it should have an appropriate viscosity for the intended use. The choice of medically acceptable carriers is very wide and can include amongst others, water, aqueous solutions, syrups, alcohols, glycerine, mineral oil, vegetable oils, synthetic mucilage-like substances such as polyvinyl alcohol, carboxymethylcellulose and so on. Further examples which may be mentioned are the water soluble polymers listed by Suzuki et al. in U.S. Pat. No. 4,569,837, col. 4, lines 9 through 21. Simple saline solutions and similar aqueous solutions can be used, but may be washed out of the periodontal pocket rather quickly and easily. A preferred alternative is one of the thicker, viscous media such as carboxymethylcellulose. In general, the more viscous the medium, the better it will adhere in the periodontal pocket; however highly viscous carrier may be difficult to insert with a syringe and rubber tube and consequently may not spread through the pocket to any useful extent. An especially preferred form then is a thermally gelling polymer, such as those vehicles disclosed by Krezanowski in U.S. Pat. No. 4,188,373. The Pluronic ® series of polyoxypropylene-polyoxyethylene copolymers, marketed by BASF Wyandotte, Parsippany, N.J., contains several suitable examples. These polymers are compatible with many commonly used pharmaceutical materials, and have been approved by the FDA for medical use. The Pluronic series can be obtained in a range of molecular weights and compositions; thus the carrier formulation may be tailored for optimum performance in the environment of the invention. FIG. 2 shows graphically the gelling temperature of aqueous Pluronic F127 solutions of different concentrations. Because of hydrogen bonding, the viscosity of the solutions increases greatly with temperature. Pluronic concentrations of 20 wt% have ideal characteristics, being free-flowing fluids at room temperature, but gelling rapidly at 30° C. or above. Thus these solutions are amenable to delivery by the syringe/rubber tube method, but quickly take on the necessary viscosity for good adhesion and durability once resident within the periodontal pocket. Optionally, a self-gelling preparation such as those disclosed by Caslavsky et al. in U.S. Pat. No. 4,563,351 (January 1986) could be used for the carrier medium.

EXAMPLE 1

Figure 3:
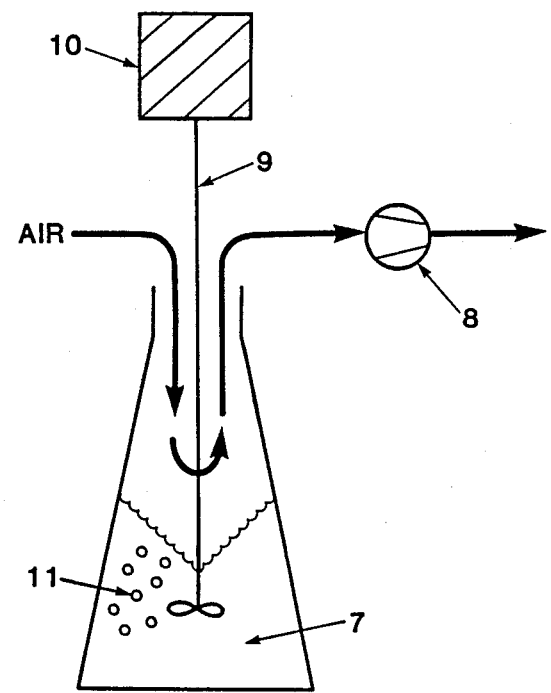
FIG. 3 shows the solvent evaporation technique used to prepare microparticles.

Polycarbonate was used to prepared microparticles by the solvent evaporation process. The drug used was tetracycline free base (TFB). The aqueous phase was saturated with TFB before starting a microparticle preparation run. In this way migration of the TFB into the aqueous phase during particle formation was minimized, and it was possible to encapsulate 70 to 100% of the tFB used. FIG. 3 shows the apparatus used to prepare the microparticles. Known amounts of TFB and polycarbonate dissolved in methylene chloride were added to the aqueous phase 7 containing polyvinyl alcohol (PVA) and 3 ppm n-octanol. The PVA is an emulsifier and the n-octanol an anti-foaming agent. Air was continuously passed over the solution by means of the vacuum pump 8. A stirrer 9 driven by a motor 10 kept the solution stirred and as the methylene chloride evaporated, the emulsion droplets 11 solidified. The microparticles thus formed were separated from the aqueous solution, dried and sieved to obtain three size fractions; 50–110 microns, 110–210 microns and 210–500 microns. The in vitro drug release rate was measured by dispersing a known amount of microparticles in a volume of aqueous saline solution (0.9% NaCl). The dispersion was stirred and kept at a temperature of 37° C. Samples were periodically removed and diluted and their antibiotic concentration determined by UV spectrophotometry. The total tetracycline content of the microparticles was determined in a similar way by dissolving a known amount of microparticles and measuring the antibiotic concentration. The presence of the matrix polymer in the solution does not interfere with the UV measurements. A typical result is shown by the upper curve in FIG. 4. The initial release rate was high for a couple of hours, the remained fairly steady until it tapered off at times in excess of 25 hours. Drug loadings between 18 and 35 wt% were used. The release curves for the three size fractions were closely bunched, and it appeared that the size of the microparticles is relatively unimportant as far as the drug kinetics are concerned but should be limited rather by the practical considerations of ease of manufacture, convenience of insertion and comfort in use. These experiments showed that microparticles made of polycarbonate containing 18 to 35 wt% tetracycline and ranging in size from 50 to 500 microns were capable of delivering tetracycline in a sustained fashion for periods of about 25 hours. Since the periodontal pocket is small and its fluid exchange rate slow, the flow of gingival fluid in a single periodontal pocket being of the order of 10 microliters per hour, this in vitro release rate is estimated to correspond to an in vivo release period of the order of 10 to 20 days.

EXAMPLE 2

Figure 4:
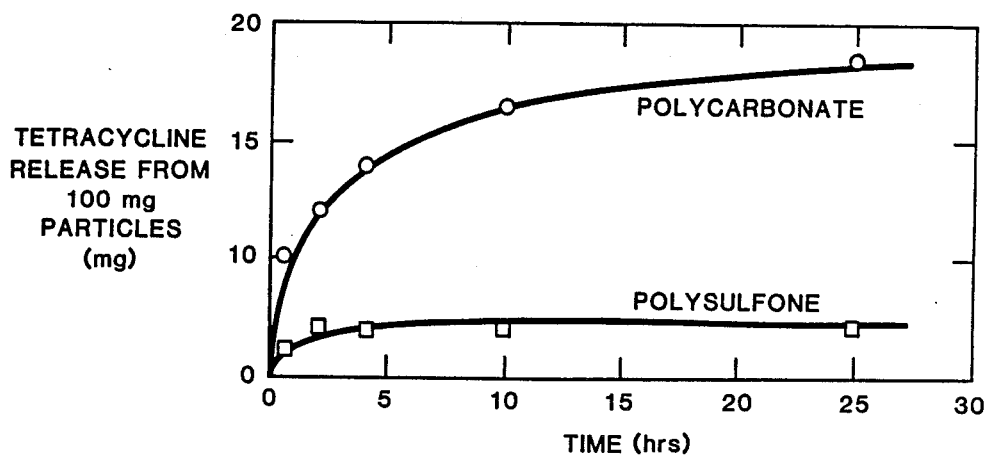
FIG. 4 is a graphic representation of the in vitro drug release rate of tetracycline from polysulfone microparticles.

The method as described in Example 1 was used to prepare microparticles. Polysulfone was chosen as the matrix material; the drug used was TFB. A typical release curve is shown in FIG. 4. As can be seen the drug release rate was very slow, only a small fraction of the total drug loading having been released after 24 hours. Although too slow to be within the parameters for optimum treatment of periodontal disease, this combination of drug and matrix would be appropriate to embodiments of the invention calling for a very small dosage level over a long time period.

EXAMPLE 3

Figure 5:
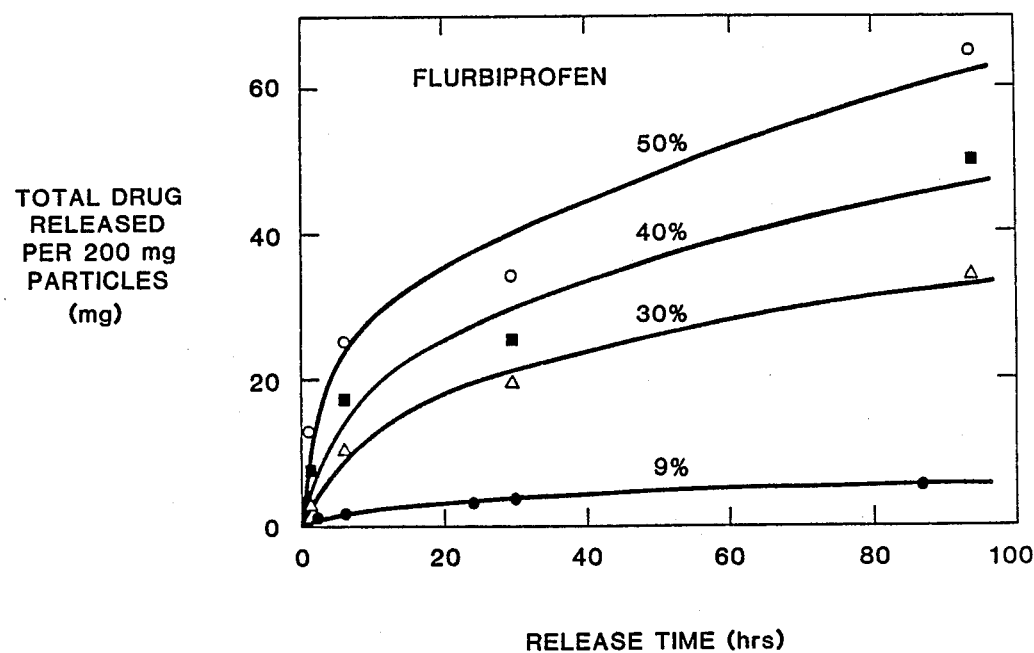
FIG. 5 is a graphic representation of the in vitro drug release rate of flurbiprofen from ethylcellulose particles.

A series of flurbiprofen microcapsules suitable for use in a periodontal formulation was prepared by the solvent evaporation method. Varying amounts of flurbiprofen were dissolved in ethylcellulose (medium ethoxy, viscosity 100 (Dow Chemical Co., Midland, MI) in MeCl₂ solution. Fifteen ml of this solution were emulsified in 600 ml of aqueous 60 bloom gelatin (0.25% as an emulsifier) being stirred at 500 rpm. Two drops of octanol were also added to eliminate any foam. The MeCl₂ was allowed to evaporate at 30° C. After 55 minutes the stirrer was shut off and the mixture was allowed to settle. The hollow capsules floating on the surface were decanted and the remaining capsules were collected on fine filter paper using a buchner funnel. The capsules were then placed in a foil dish in a dehumidifying cabinet. The drug release rates of the ethylcellulose capsules with varying drug contents were measured. These results are shown in FIG. 5. The flurbiprofen content of various batches of microcapsules is also shown on this figure. As shown, the microcapsule delivery rate can be varied over a wide range by varying the drug to polymer ratio in the microcapsules.

I claim:

1. A controlled release drug delivery system for placement in a periodontal pocket, comprising:
   (a) a plurality of discrete microparticles comprising a drug-containing polymer and the drug contained therein, said microparticles being between 10 and 500 microns in diameter, and
   (b) a fluid suspending medium for said microparticles; said drug delivery system remaining active in the periodontal pocket for a period of between one and 30 days.

2. The delivery system of claim 1, wherein the drug is selected from the group consisting of antimicrobial drugs, anti-inflammatory drugs and local anaesthetics.

3. The delivery system of claim 1, wherein the drug is an antibiotic.

4. The delivery system of claim 1, wherein the drug is chosen from the group consisting of tetracycline, its compounds and derivatives.

5. The delivery system of claim 1, wherein the drug is chosen from the group consisting of chlorhexidine, its compounds and derivatives.

6. The delivery system of claim 1, wherein the drug is flurbiprofen.

7. The delivery system of claim 1, wherein said drug-containing polymer is chosen from the group consisting of cellulose acetate, ethylcellulose, polystyrene, polysulfone, polycarbonate and lacticglycolic acid copolymers.

8. The delivery system of claim 1, wherein said drug-containing polymer is polycarbonate.

9. The delivery system of claim 1, wherein said drug-containing polymer is chosen from the group consisting of lacticglycolic acid copolymers.

10. The delivery system of claim 1, wherein the fluid suspending medium has a viscosity of at least 1000 centipoise.

11. The delivery system of claim 1, wherein the fluid suspending medium is a thermally gelling fluid, said fluid having a sol/gel transition temperature between 25° and 40° C. and being a free-flowing liquid below the transition temperature and a thickened non-flowing gel above the transition temperature.

12. A method for treating periodontal disease comprising inserting into a periodontal pocket a controlled release drug delivery system comprising:
   (a) a plurality of discrete microparticles comprising a drug-containing polymer and the drug contained therein, said microparticles being between 10 and 500 microns in diameter, and
   (b) a fluid suspending medium for said microparticles; said drug delivery system remaining active in the periodontal pocket for a period of between one and 30 days.

* * * * *